(12) United States Patent
Hatanaka (10) Patent No.: US 10,824,835 B2
(45) Date of Patent: Nov. 3, 2020

(54) ELECTRONIC DEVICE

(71) Applicant: FUJITSU CONNECTED TECHNOLOGIES LIMITED, Kawasaki (JP)

(72) Inventor: Takahiro Hatanaka, Inagi (JP)

(73) Assignee: FUJITSU CONNECTED TECHNOLOGIES LIMITED, Kawasaki (JP)

( * ) Notice: Subject to any disclaimer, the term of this patent is extended or adjusted under 35 U.S.C. 154(b) by 87 days.

(21) Appl. No.: 16/155,110

(22) Filed: Oct. 9, 2018

(65) Prior Publication Data

US 2019/0114456 A1    Apr. 18, 2019

(30) Foreign Application Priority Data

Oct. 12, 2017  (JP) ................................ 2017-198540

(51) Int. Cl.
*G06K 9/00* (2006.01)
*A61B 5/117* (2016.01)

(52) U.S. Cl.
CPC ............ *G06K 9/0002* (2013.01); *A61B 5/117* (2013.01)

(58) Field of Classification Search
CPC ...... G06K 9/00; G06K 9/0004; G06K 9/0002; G06K 9/0012; G06K 9/00033; G06K 9/00046; G06K 2009/0006; A61B 5/117; A61B 5/1172
USPC ...................................................... 382/125
See application file for complete search history.

(56) References Cited

U.S. PATENT DOCUMENTS

| | | | |
|---|---|---|---|
| 2003/0194114 A1* | 10/2003 | Mitsuyu | G06K 9/00026 382/124 |
| 2004/0065915 A1 | 4/2004 | Honda | |
| 2007/0019844 A1* | 1/2007 | Yumoto | G06K 9/00087 382/124 |
| 2008/0025582 A1* | 1/2008 | Kobayashi | G06K 9/00013 382/124 |
| 2011/0193727 A1* | 8/2011 | Goto | G06F 3/03547 341/20 |
| 2012/0237091 A1* | 9/2012 | Nakamura | G06T 1/00 382/124 |
| 2017/0031497 A1* | 2/2017 | Kono | G06F 3/0416 |

FOREIGN PATENT DOCUMENTS

| | | |
|---|---|---|
| JP | 2003-282609 A | 10/2003 |
| JP | 2005-301658 A | 10/2005 |
| JP | 2005-338980 A | 12/2005 |
| JP | 2007-201477 A | 8/2007 |

* cited by examiner

*Primary Examiner* — Ali Bayat
(74) *Attorney, Agent, or Firm* — Westerman, Hattori, Daniels & Adrian, LLP (57) ABSTRACT

An electronic device includes: an operation unit including a fingerprint sensor, a longitudinal direction of the operation unit being defined as a first direction; and a processor that performs fingerprint authentication processing and processing to respond to movement of a finger of a user in the first direction on the operation unit, based on a detection result by the fingerprint sensor, in which a sensing unit of the fingerprint sensor is displaced from the center of the operation unit in the first direction.

9 Claims, 12 Drawing Sheets

ELECTRONIC DEVICE

CROSS-REFERENCE TO RELATED APPLICATION

This application is based upon and claims the benefit of priority of the prior Japanese Patent Application No. 2017-198540, filed on Oct. 12, 2017, the entire contents of which are incorporated herein by reference.

FIELD

The embodiments discussed herein are related to an electronic device.

BACKGROUND

In known technique, an electronic device has, on its side surface, an operation unit having a fingerprint sensor and implements a screen scroll function in a display unit based on the operation by the movement of a user's finger on the operation unit.

Note that techniques relating to the present application are disclosed in Japanese Laid-open Patent Application Publication No. 2005-301658.

However, in the conventional technique as described above, in the case of using a fingerprint sensor having a sensing unit shorter than the length of the operation unit in the longitudinal direction, it is difficult to enhance ease of operation by the movement of the user's finger on the operation unit. To enhance the ease of operation described above, it is effective to make longer to an extent, the length of the operation unit in the direction corresponding to the movement of the finger and also to make longer in the same direction, the effective area of the fingerprint sensor in the operation unit (in other words, the contact area touched by the user's finger where the fingerprint sensor may function). In this point, there are some cases where it is difficult to provide a fingerprint sensor having a sensing unit with the same size as the length of operation unit in the longitudinal direction, from the viewpoints such as the versatility and cost of the fingerprint sensor and the allocation of a wiring space for the fingerprint sensor. If a fingerprint sensor having a sensing unit significantly shorter than the length of the operation unit in the longitudinal direction is used, the effective area of the fingerprint sensor in the operation unit covers only a partial area of the operation unit, and this may decrease ease of the operation.

SUMMARY

According to an aspect of the embodiments, an electronic device includes: an operation unit including a fingerprint sensor, a longitudinal direction of the operation unit being defined as a first direction; and a processor that performs fingerprint authentication processing and processing to respond to movement of a finger of a user in the first direction on the operation unit, based on a detection result by the fingerprint sensor, in which a sensing unit of the fingerprint sensor is displaced from the center of the operation unit in the first direction.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Hereinafter, each embodiment will be described in detail with reference to the drawings.

Figure 1A:
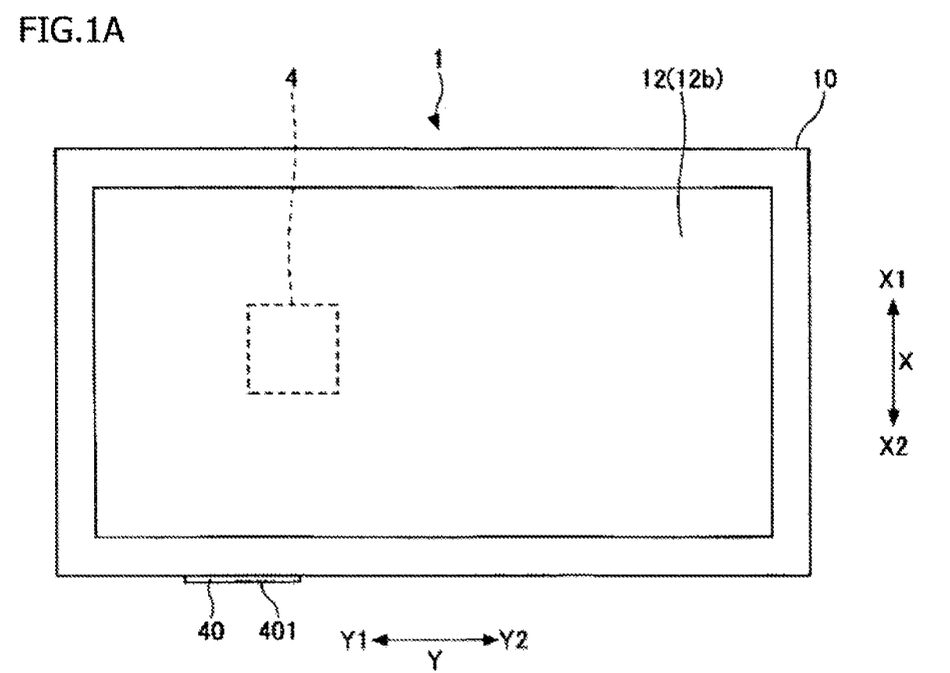
FIG. 1A is a schematic plan view of the appearance of an electronic device 1 according to an embodiment.
Figure 1B:
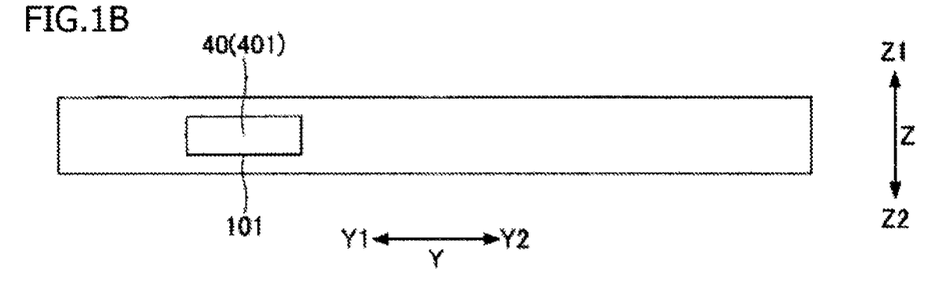
FIG. 1B is a schematic side view of the same.

FIG. 1A is a schematic plan view of an appearance of an electronic device 1 of an embodiment, and FIG. 1B is a schematic side view of the same. In FIGS. 1A and 1B, the X direction, the Y direction (an example of a first direction), and the Z direction, which are three directions orthogonal to each other, are defined. In the following, the short-side direction of the electronic device 1 is defined as the X direction; the longitudinal direction of the electronic device 1, the Y direction; and the thickness direction of the electronic device 1, the Z direction, for explanation. In the following, the Y1 side of the Y direction is defined as "the upper side of the screen (the far side of the lower end of the screen)"; and the Y2 side of the Y direction, "the lower side of the screen (the near side of the lower end of the screen)", for explanation. The Z1 side of the Z direction is defined as the "the upper side". In the following, unless otherwise mentioned, the upper surface portion of the device means the portion that provides the surface of the upper side of the electronic device 1. The side surface portion of the device means, unless otherwise mentioned, a portion that is part of the electronic device 1 and provides a surface having the normal line perpendicular to the Z direction. The same applies to the bottom surface portion and other portions of the device.

Although the electronic device 1 is of a portable type but may be of a fixed type. The portable electronic device 1 may be a smartphone, mobile phone, PDA (personal digital assistant), portable information terminal such as a tablet PC, portable game machine, portable music player, wristwatch type wearable terminal, or the like.

The electronic device 1 includes a housing 10 and a top plate member 12.

The housing 10 is made of, for example, resin. The housing 10 includes the side surface portion of the device and the bottom surface portion of the device (the lower surface portion of the device). The housing 10 may also include part of the upper surface portion of the device (the outer periphery of the top plate member 12). In the following, the inside of the housing 10 means a space on the device center side of the side surface portion of the device, the bottom surface portion of the device, and the upper surface portion of the device. Various electronic components such as a processor 4 (which is schematically illustrated in FIG. 1A by the dotted lines) are mounted inside the housing 10.

The top plate member 12 is a surface member forming the upper surface portion of the device. The top plate member 12 is a top plate member used for, for example, a liquid crystal panel unit, an organic EL (electro luminescence) panel unit, or the like. Note that the top plate member 12 may include a touch panel integrally. In this embodiment, as an example, the top plate member 12 is a glass plate which covers the upper side of a liquid crystal panel unit 12*b* (an example of a display unit) inside the housing 10.

The electronic device 1 includes the processor 4 (schematically illustrated in FIG. 1 by the dotted lines), which implements various functions, inside the housing 10. The processor 4 is a computer, which may be implemented with, for example, an IC (integrated circuit) package, such as an LSI (large-scale integration), mounted on a circuit board (not illustrated). Note that the processor 4 may be implemented with multiple computers that work cooperatively.

The processor 4 performs fingerprint authentication processing and processing to respond to movement of a user's finger in the Y direction on a side key 40, based on a fingerprint image from a fingerprint sensor 42 described later (the finger print image is an example of a detection result of the fingerprint sensor 42). A specific example of processing by the processor 4 will be described later with reference to FIGS. 3A and 3B.

The electronic device 1 includes the side key 40 (an example of an operation unit) on the side surface portion of the device. The side key 40 is provided such that its surface 401 is exposed through an opening 101 formed in the side surface portion of the device (see also FIG. 2). Here, in the state where the side key 40 is not pushed in, the side key 40 may protrude slightly from the side surface portion of the device as illustrated in FIG. 1A. However, in other embodiments, the side key 40 may be provided to be flush with the side surface portion of the device.

The side key 40 is capable of receiving a push-in operation (pressing operation). In other words, the side key 40 may move in the X direction (the direction perpendicular to the side surface portion of the device). The push-in operation of the side key 40 in the X1 direction may trigger any function, which may be, for example, a function to power on and off the electronic device 1, an adjustment function such as turning up and down the volume, or the like. Note that in modifications, the side key 40 may be incapable of receiving push-in operation. In other words, the side key 40 may be fixed to the side surface portion of the device.

The side key 40 provides the surface 401 which is capable of receiving slide operation (or tracing operation, hereinafter representatively referred to as slide operation) in the Y direction by a user's finger. In the following, ease of operation of the side key 40 means, unless otherwise mentioned, ease of operation of a slide operation of the side key 40 in the Y direction. In other words, ease of operation of the side key 40 means, unless otherwise mentioned, ease of operation of a slide operation of the side key 40 in the longitudinal direction. The side key 40 has a configuration in which the longitudinal direction is defined as the Y direction, to enhance ease of operation. The side key 40 is, for example, longer than or equal to 15 mm in the Y direction. Note that the dimension in each short-side direction (dimension in the thickness direction of the electronic device 1) of the side key 40 practically depends on the thickness or other factors of the electronic device 1.

The side key 40 has the fingerprint sensor 42. The fingerprint sensor 42 acquires fingerprint images. The fingerprint sensor 42 may be of any type, such as an electrostatic type. However, the fingerprint sensor 42 is not of a type that needs tracing of the user's finger to acquire (read) a fingerprint image (in other words, a sweep type).

Figure 2:
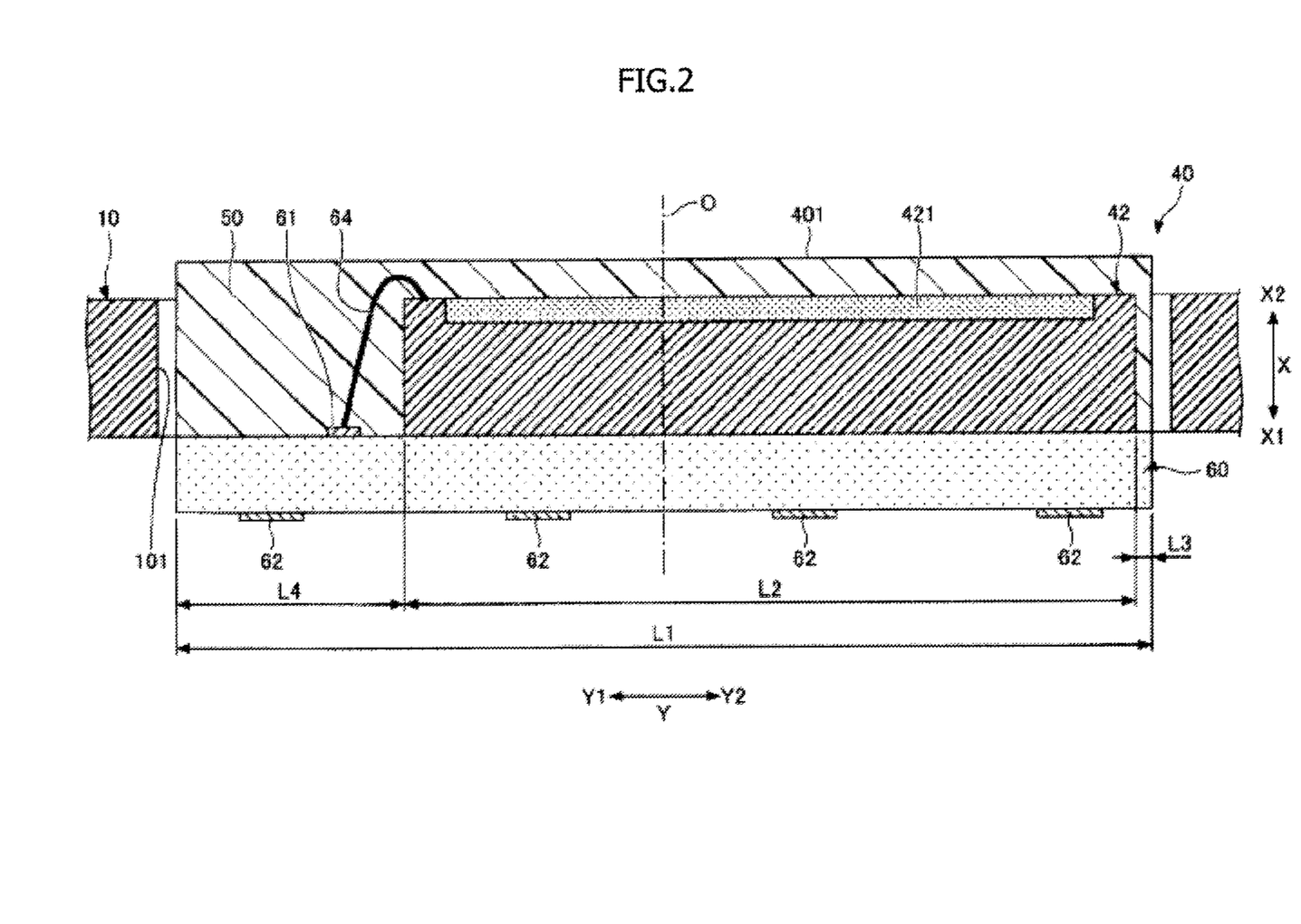
FIG. 2 is a schematic cross-sectional view of part of the electronic device 1 taken along an XY plane passing through a side key.

For example, the fingerprint sensor 42 is in a form of an IC chip provided near the surface 401 of the side key 40 on the X2 side and has a large number of metal electrodes arrayed on the surface on the X2 side of the IC chip as a sensing unit 421 (see FIG. 2). When electrical current is applied to the surface 401 of the side key 40 in the state where the user's finger is put on the surface 401 of the side key 40, the metal electrodes of the sensing unit 421 and the surface of the finger form capacitors, which store electric charge according to the irregularities of the finger. A relatively large amount of electric charge is stored where the distance between an electrode and the finger surface is small, and a relatively small amount of electric charge is stored where the distance is large. The electric charge is read out from each metal electrode and, for example, converted from analog to digital into 8-bit (=256) gradations, and thus a fingerprint image is acquired. For example, 256×300=76, 800 metal electrodes are arrayed at intervals of 50 μm (500 dpi). In this case, because intervals of irregularities of a finger print are approximately 200 μm, a fingerprint image thus obtained has sufficient resolution for fingerprint authentication.

Note that in this embodiment, as an example, the side key 40 is provided on the X2 side, which is the left side for the user who is looking at the screen. Accordingly, the user may touch the side key 40 with the thumb of the left hand, while holding the electronic device 1 with the left hand. In this case, fingerprint authentication and slide operation may be performed by the thumb of the left hand. Alternatively, the user may touch the side key 40 with the index finger or another finger of the right hand routed via the bottom surface portion of the device, while holding the electronic device 1 with the right hand. In this case, fingerprint authentication and slide operation may be performed by the index finger or another finger of the right hand. However, in modifications, the side key 40 may be provided on the other side (X1 side) or on each of the both sides.

FIG. 2 is a schematic cross-sectional view of part of the electronic device 1 taken along an XY plane passing through the side key 40. In FIG. 2, center line O passing through the center of the side key 40 in the Y direction (center line O extending in the X direction) is illustrated. Note that the side key 40 may have a flange or the like to prevent it from coming off, and a waterproofing mechanism may be provided between the side key 40 and the housing 10. These are not illustrated in FIG. 2 because FIG. 2 is a schematic view.

In this embodiment, as an example, the side key 40 incorporates the fingerprint sensor 42. In other words, the side key 40 is formed as a sensor package integrally including the fingerprint sensor 42. Specifically, the fingerprint sensor 42 in the side key 40 is sealed with resin (for example, epoxy resin). In FIG. 2, a resin portion 50 for sealing is illustrated, and the fingerprint sensor 42 is embedded in the resin portion 50. The surface 401 of the side key 40 is part of the resin portion 50. In this embodiment, as an example, the resin portion 50 includes the surface of the entire portion of the side key 40 that is exposed from the side surface portion of the device at the time when the side key 40 is not pushed in. Here, the surface of the resin portion 50 that is visible from the outside of the device (such as the surface 401 of the side key 40) may be, for example, painted for design.

In this embodiment, as an example, the fingerprint sensor 42 is in a form of an IC chip, which is mounted on a circuit board 60. As described above, the fingerprint sensor 42 has the sensing unit (active area) 421 where a large number of metal electrodes (not illustrated) are arrayed. The sensing unit 421 extends over almost the entire surface of the fingerprint sensor 42 on the X2 side. In this embodiment, as an example, the center of the sensing unit 421 is aligned with the center of the fingerprint sensor 42 in the Y direction. However, the sensing unit 421 may be displaced a little on the Y2 side from the center of the fingerprint sensor 42 in the Y direction because electrodes (not illustrated) for connection with wires 64 are arranged on the X2 side of the surface. Note that in this embodiment, as an example, "the length of the fingerprint sensor 42 in the Y direction (see L2 in FIG. 2)" is almost the same as the length of the sensing unit 421 in the same direction. In other words, the length of the fingerprint sensor 42 in the Y direction practically depends on the length of the sensing unit 421 in the same direction, and the difference between these lengths is very small. For this reason, in the following, explanation for the length of the fingerprint sensor 42 in the Y direction may be read as explanation for the length of the sensing unit 421.

The fingerprint sensor 42 is electrically connected to electrodes 61 on the circuit board 60 on the Y1 side in the Y direction. For the electrical connection with the electrodes 61, for example, wire bonding (see the wires 64) is used. Note that the circuit board 60 is electrically connected to, for example, an FPC (flexible printed circuit) (not illustrated) via electrodes 62 on the X1 side surface and thus electrically connected to the processor 4 via the FPC.

The resin portion 50 is formed by, for example, molding. As illustrated in FIG. 2, the resin portion 50 is bonded to the X2 side surface of the circuit board 60 and includes the fingerprint sensor 42 and the wires 64 inside. Note that the resin portion 50 may be formed to be bonded to side surfaces of the circuit board 60.

In this embodiment, the side key 40 is longer than the sensing unit 421 of the fingerprint sensor 42 in the Y direction. In other words, the length L1 of the side key 40 is longer than the length L2 of the fingerprint sensor 42. Thus, the sensing unit 421 of the fingerprint sensor 42, when viewed in the X direction, does not overlap with the entire surface 401 of the side key 40 but part of the surface 401.

In this embodiment, the sensing unit 421 of the fingerprint sensor 42 is displaced from the center of the side key 40 (see center line O) to the Y2 side in the Y direction. In other words, the center of the sensing unit 421 in the Y direction is displaced (decentered) from the center of the side key 40 to the Y2 side in the Y direction. For example, it is assumed that L3 is the length in the Y direction between the fingerprint sensor 42 and the edge of the side key 40 on the Y2 side in the Y direction, and L4 is the length in the Y direction between the fingerprint sensor 42 and the edge of the side key 40 on the Y1 side in the Y direction. Here, the relationship L3<L4 holds. This enhances ease of operation as described later.

Note that as for the Z direction, the center of the sensing unit 421 of the fingerprint sensor 42 may be aligned with the center of the side key 40 in the Z direction.

Figure 3A:
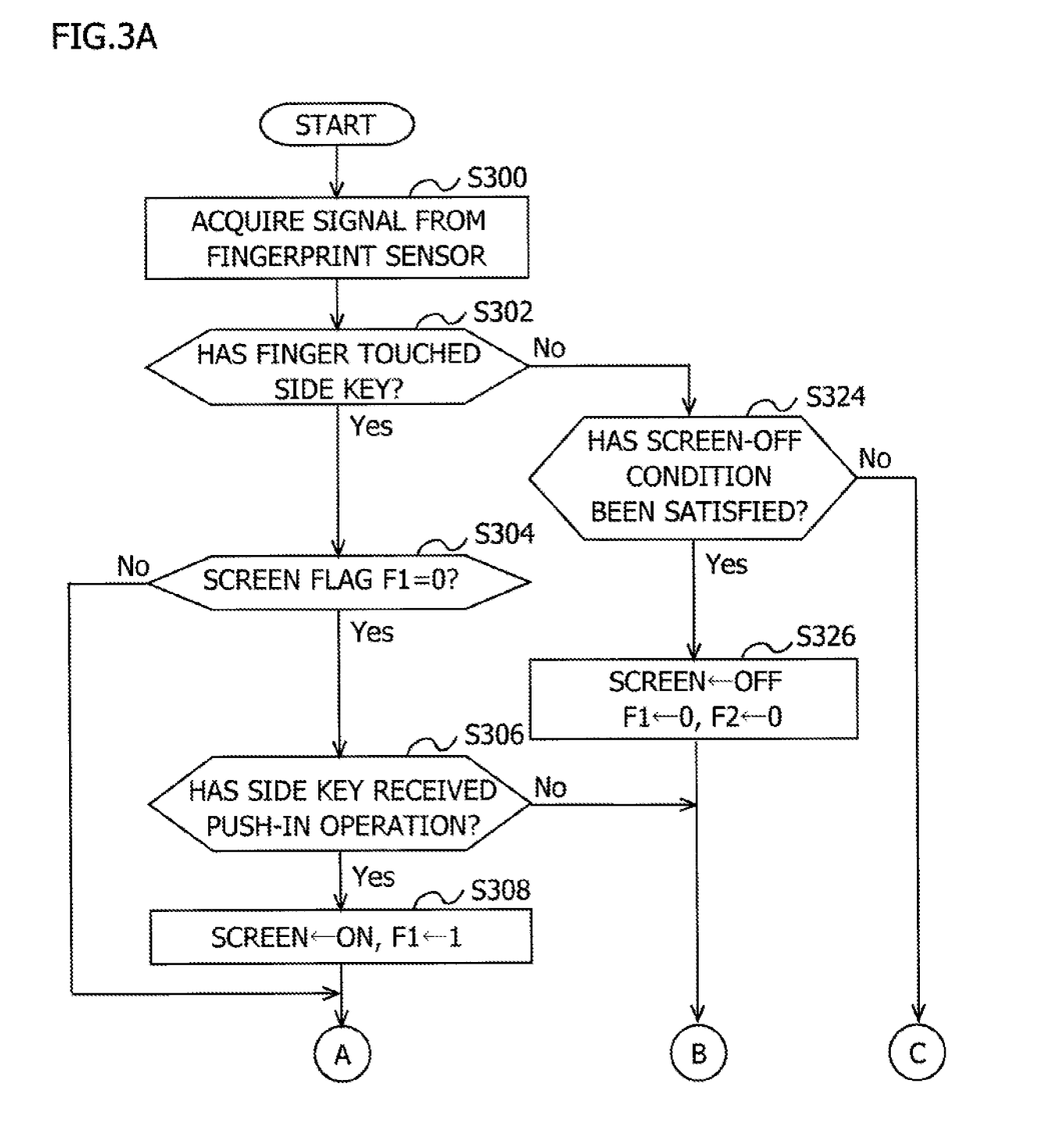
FIGS. 3A and 3B are a brief flowchart of an example of processing executed by a processor.
Figure 3B:
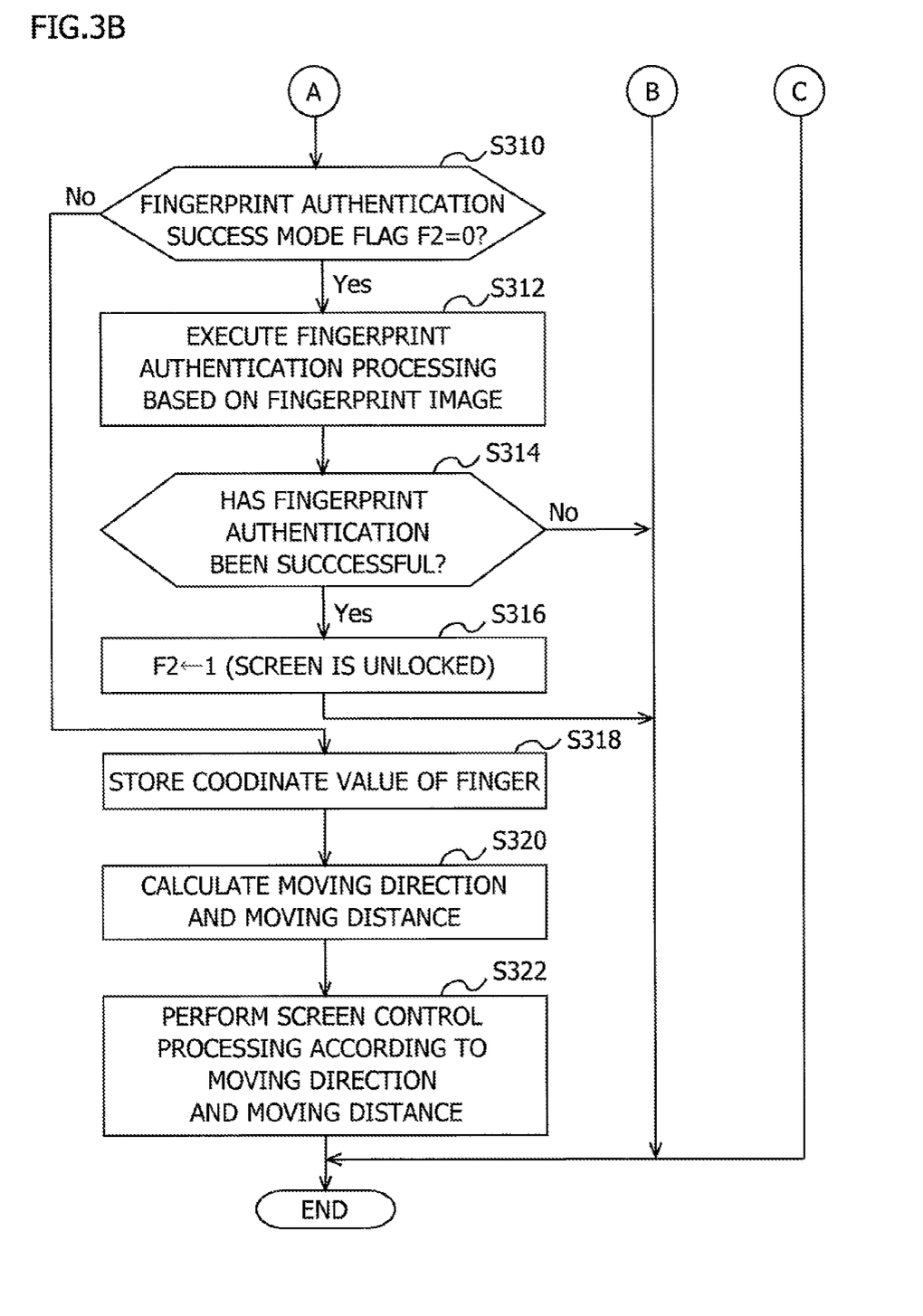

FIGS. 3A and 3B are a brief flowchart of an example of processing executed by the processor 4.

At step S300, the processor 4 acquires a signal from the fingerprint sensor 42. Note that when the fingerprint sensor 42 has acquired a fingerprint image, the processor 4 acquires the fingerprint image as a signal from the fingerprint sensor 42.

At step S302, based on the signal acquired at step S300, the processor 4 determines whether a finger has touched the side key 40. In FIGS. 3A and 3B, as an example, when the fingerprint sensor 42 has acquired a fingerprint image, the processor 4 determines that a finger has touched the side key 40. If the determination result is "YES", the process proceeds to step S304, and if not, to step S324.

At step S304, the processor 4 determines whether screen flag F1 is "0". If screen flag F1 is "0", it means the screen is currently off. The initial value of screen flag F1 (the value set when the electronic device 1 is turned on) is "1". If the determination result is "YES", the process proceeds to step S306, and if not, to step S310.

At step S306, the processor 4 determines whether the side key 40 has received a push-in operation. The push-in operation of the side key 40 may be determined based on the state of a switch (not illustrated) provided on the X1 side of the side key 40. If the determination result is "YES", the process proceeds to step S308, and if not, the processing in this cycle ends without doing anything.

At step S308, the processor 4 turns on the screen and sets screen flag F1 to "1".

At step S310, the processor 4 determines whether fingerprint authentication success mode flag F2 is "0". If fingerprint authentication success mode flag F2 is "0", it means that the fingerprint authentication has not been successful. The initial value of fingerprint authentication success mode flag F2 (the value when the electronic device 1 is turned on) is "0". If the determination result is "YES", the process proceeds to step S312, and if not, to step S318.

At step S312, the processor 4 executes fingerprint authentication processing based on the fingerprint image acquired at step S300. In the fingerprint authentication processing, consistency is checked between the fingerprint image acquired at step S300 and a fingerprint image registered in advance in a storage (not illustrated) of the processor 4. Any method may be used for the detailed algorithm of the fingerprint authentication processing, including pattern matching and comparison of only feature data.

At step S314, the processor 4 determines whether the fingerprint authentication has been successful. In other words, the processor 4 determines whether the fingerprint image acquired at step S300 has been found to be consistent with the fingerprint image registered in advance. If the determination result is "YES", the process proceeds to step S316, and if not, the processing in this cycle ends without doing anything.

At step S316, the processor 4 sets fingerprint authentication success mode flag F2 to "1". If fingerprint authentication success mode flag F2 is "1", it means that the fingerprint authentication has been successful, and the screen is currently unlocked. Note that here, the processor 4 may store the fingerprint image acquired at step S300 as an initial image (previous image).

At step S318, the processor 4 stores the fingerprint image acquired at step S300 (current image).

At step S320, the processor 4 calculates the moving direction and moving distance of the finger in the Y direction. The moving direction and moving distance of the finger may be derived, for example, based on the previous image and the current image of the fingerprint image. Specifically, the moving direction and moving distance of the finger may be derived by calculating positional difference between temporally successive fingerprint images (finger position shift).

At step S322, the processor 4 performs screen control processing based on the moving direction and moving distance obtained at step S320. The screen control processing is, for example, at least one of scroll processing to scroll an image in the screen, transition processing to cause screen transition, and zoom-in/zoom-out processing to zoom in and out on an image in the screen. Although the kind of the image in the screen depends on an application being executed, it is, for example, a map image.

At step S324, the processor 4 determines whether a screen-off condition has been satisfied. The screen-off condition may be any condition. For example, the screen-off condition is satisfied when the non-operation state continues for a specified time. If the determination result is "YES", the process proceeds to step S326, and if not, the processing in this cycle ends without doing anything.

At step S326, the processor 4 turns off the screen, resets screen flag F1 to "0", and also resets fingerprint authentication success mode flag F2 to "0".

In the processing illustrated in FIGS. 3A and 3B, processing to respond to the movement of the user's finger on the side key 40 in the Y direction (screen control processing in FIGS. 3A and 3B) is performed. In addition, processing to respond to push-in operation of the side key 40 is performed. In other words, the screen is turned on at a push-in operation of the side key 40 as a trigger.

Note that although in FIGS. 3A and 3B, the fingerprint sensor 42 functions even when the screen is off, as an example, the present disclosure is not limited to this operation. In other words, the fingerprint sensor 42 may be activated when the screen is turned on (see step S308).

Next, effects of this embodiment will be described with reference to FIGS. 4 to 9.

Figure 4:
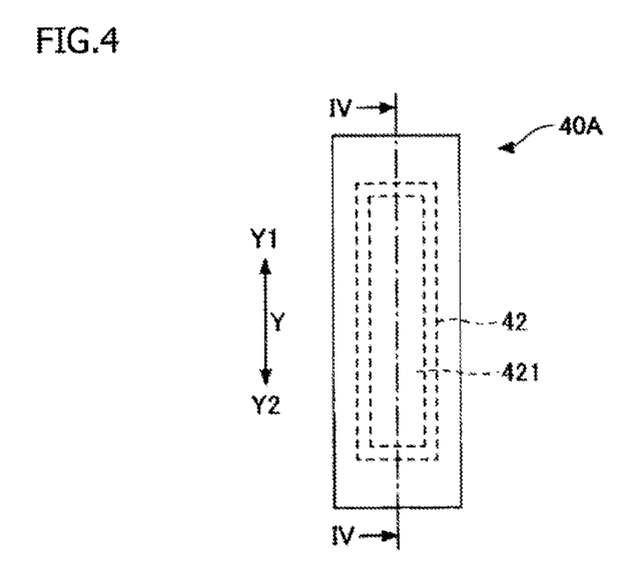
FIG. 4 is a diagram for explaining a configuration of a comparative example.
Figure 5:
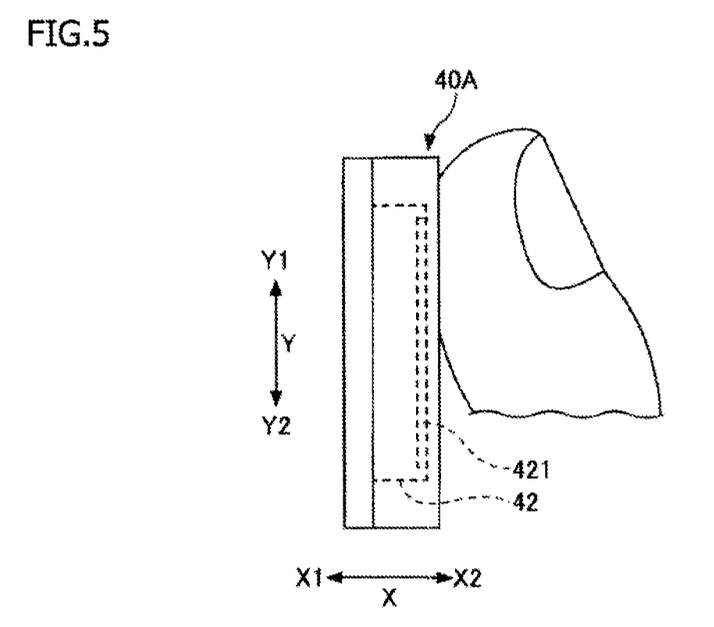
FIG. 5 is a cross-sectional view of the comparative example in a state where a finger is on the Y1 side.
Figure 6:
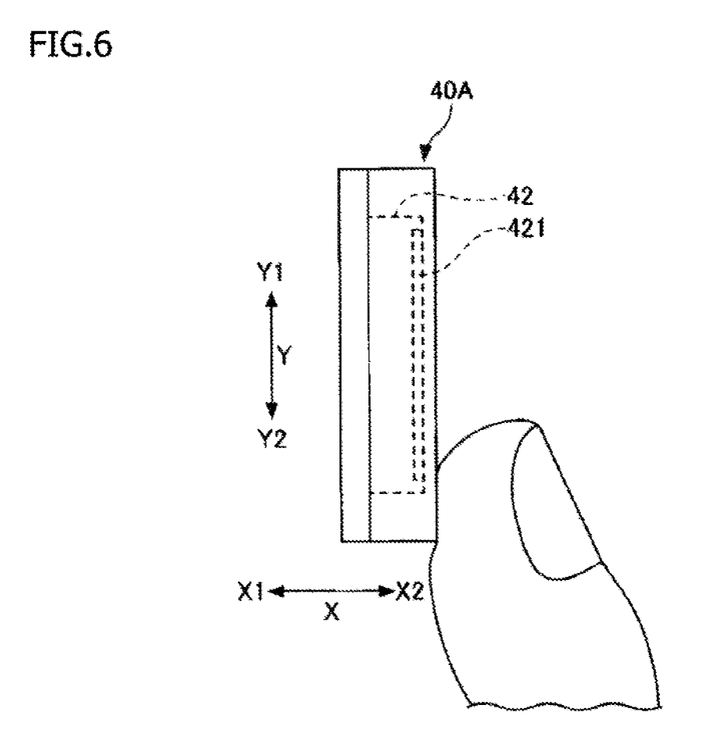
FIG. 6 is a cross-sectional view of the comparative example in a state where the finger is on the Y2 side.
Figure 7:
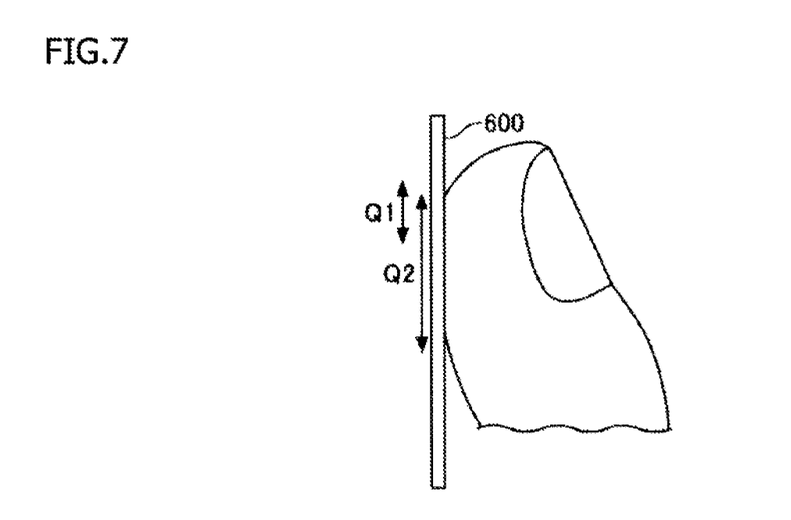
FIG. 7 is a diagram for explaining difference between the contact position of a finger and the user's feeling.
Figure 8:
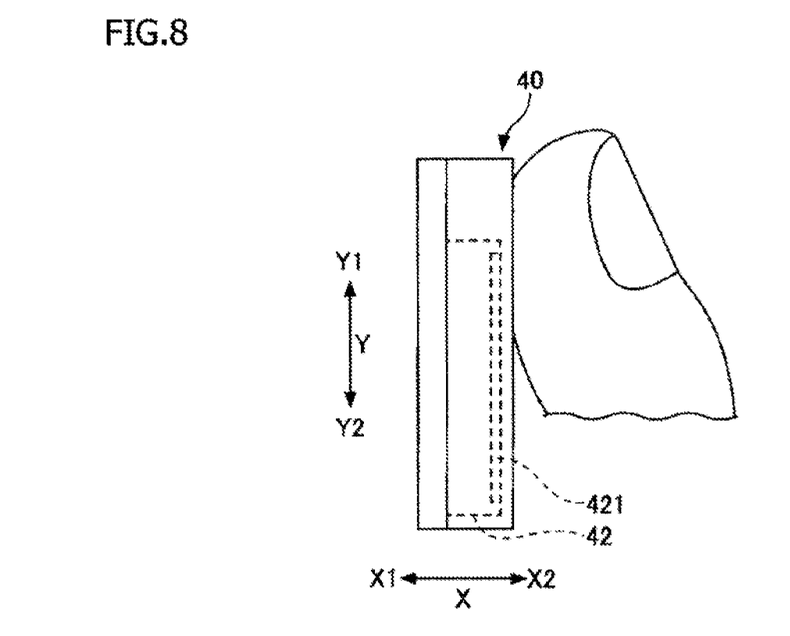
FIG. 8 is a cross-sectional view of the side key in this embodiment when the finger is on the Y1 side.
Figure 9:
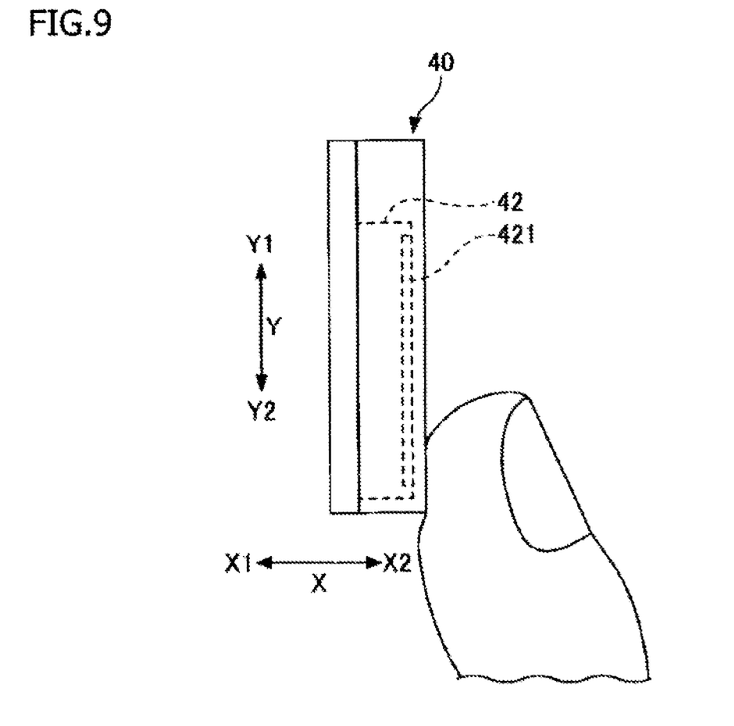
FIG. 9 is a cross-sectional view of the side key in this embodiment when the finger is on the Y2 side.

FIGS. 4 to 6 are diagrams for explaining a comparative example. FIG. 4 is a plan view, and FIGS. 5 and 6 are cross-sectional views taken along line IV-IV in FIG. 4. FIG. 5 illustrates a state where a finger is on the Y1 side, and FIG. 6 illustrates a state where the finger is on the Y2 side. FIG. 7 is a diagram for explaining difference between the contact position of a finger and the user's feeling, and FIG. 7 is a side view of a finger on an operation surface 600. FIGS. 8 and 9 are cross-sectional views of the side key 40 according to this embodiment. FIG. 8 illustrates a state where a finger is on the Y1 side, and FIG. 9 illustrates a state where the finger is on the Y2 side. Note that in FIGS. 8 and 9, illustration of the wires 64 and other parts is omitted.

Here, as a general usage mode, it is assumed that a user holds the electronic device 1 with the left hand and performs a slide operation, while touching the side key 40 with the thumb of the left hand. In this case, the direction of the thumb is approximately in parallel with the Y direction, and the tip of the thumb is on the Y1 side in the Y direction. Hereinafter, a finger means a thumb unless otherwise mentioned.

As for the side key 40A in the comparative example, unlike this embodiment, the center of the fingerprint sensor 42 (and the sensing unit 421 thereof, the same applies in the following) is aligned with the center of the side key 40 in the Y direction. In this case, when the finger is at the position indicated in FIG. 5, the fingerprint sensor 42 is capable of acquiring a fingerprint image, but when the finger is at the position indicated in FIG. 6, the fingerprint sensor 42 is incapable of acquiring a fingerprint image. This is because when the finger is at the position indicated in FIG. 6, the finger is positioned on the Y2 side of the sensing unit 421 of the fingerprint sensor 42.

Thus, in the comparative example, the effective area of the fingerprint sensor 42 (the contact area of the user's finger where the fingerprint sensor 42 functions) is limited to part of the side key 40A in the Y direction. Specifically, the effective area of the fingerprint sensor 42 is not formed at the end portion of the side key 40A on the Y2 side in the Y direction, and the end portion of the side key 40A on the Y2 side in the Y direction is an insensitive area. For this reason, in the comparative example, the movement range within which the slide operation may be performed is incapable being maximized compared to the length of the side key 40A in the Y direction, decreasing ease of the operation. For example, this structure may cause a burden such as needing the user to repeat the slide operation more than twice, when the user performs an operation involving a longer length of slide operation.

Here, as illustrated in FIG. 7, as a typical tendency of users, there is significant difference (deviation) between range Q1 which the user feels that the user is touching on the operation surface 600 and range Q2 which the finger is actually touching on the operation surface 600. Specifically, the user tends to feel that the user is touching a range on the fingertip side more than range Q2 which the finger is actually touching. The user tends to feel that the finger is touching the fingerprint sensor 42 when the finger is at the position in FIG. 6.

For this reason, as for the comparative example, the end portion of the side key 40A on the Y2 side in the Y direction is the insensitive area, causing the user to feel a sense of incongruity, and decreasing ease of the operation. Specifically, since when the finger is at the position in FIG. 6, the range (see Q1 in FIG. 7) that the use feels that the user is touching with the finger is on the side key 40A, the user tends to expect that the user is capable of performing the slide operation even when the finger is at the position in FIG. 6. However, the finger illustrated in FIG. 6 is actually positioned in the insensitive area as described above, the user is incapable of performing the slide operation when the finger is at the position in FIG. 6. As a result, the user feels a sense of incongruity, decreasing ease of operation. In addition, the user feels that the fingerprint sensor 42 responds when the finger is on the screen upper side of the side key 40A and that the fingerprint sensor 42 does not respond when the finger is on the screen lower side of the side key 40A. Thus, the user may feel a sense of incongruity as if the response of the fingerprint sensor 42 is not symmetric with respect to the center of the side key 40A in the Y direction. Note that in the case where the lengths of the side key 40A and the fingerprint sensor 42 (the sensing unit 421) in the Y direction are larger, the level of this sense of incongruity will be larger.

On the other hand, as for the side key 40 according to this embodiment, as described above, the sensing unit 421 of the fingerprint sensor 42 is displaced from the center of the side key 40 (see center line O) to the Y2 side in the Y direction. In this case, even when the finger is at the position illustrated in FIG. 9, the fingerprint sensor 42 may acquire a fingerprint image. This is because the tip of the finger is still overlapped with the sensing unit 421 of the fingerprint sensor 42 when viewed in the X direction even when the finger is at the position illustrated in FIG. 9. In addition, also when the finger is at the position illustrated in FIG. 8, the fingerprint sensor 42 may acquire a fingerprint image. This is because also when the finger is at the position illustrated in FIG. 8, the ball of the finger is overlapped with the sensing unit 421 of the fingerprint sensor 42 when viewed in the X direction. As a result, in this embodiment, the movement range within which the slide operation may be performed may be maximized compared to the length of the side key 40A in the Y direction. Thus, this embodiment provides easier operation than the comparative example does. In addition, the response of the fingerprint sensor 42 is approximately symmetric or symmetric with respect to the center of the side key 40 in the Y direction, decreasing or eliminating the sense of incongruity caused in the above comparative example.

According to this embodiment, the effective area of the fingerprint sensor 42 (in other words, the contact area of the user's finger where the fingerprint sensor 42 may acquire fingerprint images) may be formed almost over the entire surface 401 of the side key 40 in the Y direction, as described above. In other words, according to this embodiment, even if a fingerprint sensor having a length L2 significantly shorter than the length L1 of the side key 40 in the longitudinal direction (the Y direction) is used, an effective area of the fingerprint sensor 42 may be formed almost all over the side key 40 in the Y direction. This decreases or eliminates the sense of incongruity that would occur in the above comparative example, enhancing ease of the operation.

In other words, according to this embodiment, the length of the fingerprint sensor 42 in the Y direction can be reduced to be shorter than the length of the side key 40 in the Y direction without decreasing ease of the operation, enhancing the degree of freedom of the usable size of the fingerprint sensor 42.

In addition, according to this embodiment, since the sensing unit 421 of the fingerprint sensor 42 is displaced from the center of the side key 40 to the Y2 side in the Y direction, it is easy to allocate a wiring space for the fingerprint sensor 42 on the Y1 side of the fingerprint sensor 42. Note that the wiring space for the fingerprint sensor 42 means, for example, a wiring space for wires 64 (see FIG. 2) and a work space for wire bonding. In other words, according to this embodiment, even if the length of the fingerprint sensor 42 in the Y direction is reduced to be shorter than the length of the side key 40 in the Y direction to allocate the wiring space for the fingerprint sensor 42, this embodiment may keep the same level of ease of operation as the configuration, in which the length in the Y direction of the fingerprint sensor 42 is the same as the length in the Y direction of the side key 40, may achieve. This is because if the wiring space for the fingerprint sensor 42 is allocated on the Y1 side of the fingerprint sensor 42 as in this embodiment, an insensitive is unlikely to occur on the Y1 side of the fingerprint sensor 42.

Note that this embodiment enhances ease of operation, as described above, for slide operation in which the tip of a finger is positioned on the side opposite to the side (the Y2 side for the electronic device 1) to which the sensing unit 421 of the fingerprint sensor 42 is displaced. For the above electronic device 1, since the side to which the sensing unit 421 is displaced corresponds to the lower side of the screen, it is assumed that in ordinary slide operations, the tip of a finger is positioned on the upper side of the screen. However, since in a configuration in which the upper side of the screen changes depending on the orientation of the electronic device 1, the side to which the sensing unit 421 of the fingerprint sensor 42 is displaced may be opposite to the side described in the foregoing embodiment. In this case, the side key 40 may be disposed, for example, at the center of the electronic device 1 in the Y direction.

Next, referring to FIG. 2 again and also to FIG. 10A, the relationship and the like between various lengths—L1, L2, L3, and L4—will be described.

Figure 10A:
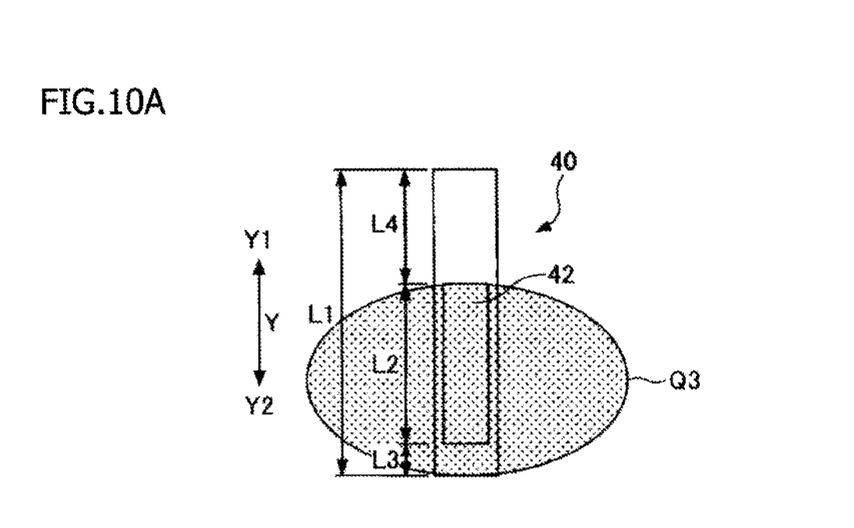
FIGS. 10A and 10B are explanatory diagrams in the case length L4 is relatively large.
Figure 10B:
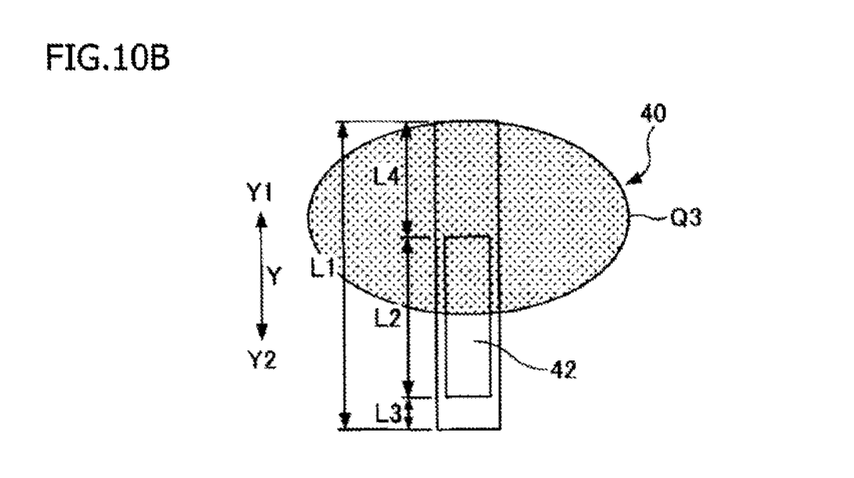
Figure 11:
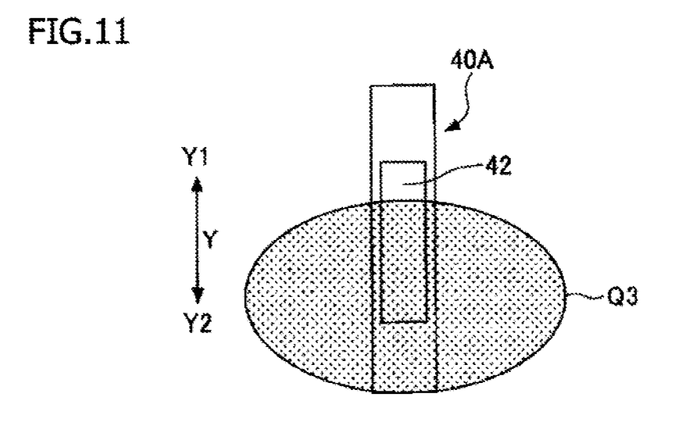
FIG. 11 is an explanatory diagram in the case of the comparative example.

FIGS. 10A and 10B, which are diagrams for explaining an inconvenience in a case where length L4 is relatively large, are plan views of the side key 40 (plan views when viewed in the X direction). FIG. 11 is a diagram for explaining a case for the comparative example. FIGS. 10A, 10B and 11 schematically illustrate the contact range Q3 of the index finger at the time when the user holds the electronic device 1 with the right hand and touches the fingerprint sensor 42 with the index finger of the right hand. In this case, the direction of the index finger is approximately perpendicular to the Y direction when viewed in the X direction. FIG. 10A illustrates a case where the contact range Q3 of the index finger is on the Y2 side, and FIG. 10B illustrates a case where the contact range Q3 of the index finger is on the Y1 side.

Meanwhile, from the viewpoint of only the fingerprint authentication processing (the operation to release the screen lock), the position of the fingerprint sensor 42 (the center position) as illustrated in the comparative example (see FIG. 4 and other figures) is more advantageous than the position in this embodiment. The reason is that, for example, contact range Q3 at the time when the user touches the fingerprint sensor 42 with the index finger of the right hand is short in the Y direction, and consequently, for the contact range Q3 illustrated in FIG. 10B, the portion of the contact range Q3 that is overlapped with the sensing unit 421 of the fingerprint sensor 42 tends to be small when viewed in the X direction.

Thus, in the case where length L4 is relatively large in this embodiment, an inconvenience of difficulty in the fingerprint authentication processing with the index finger of the right hand may occur.

In this embodiment, from the viewpoint of reducing or preventing such an inconvenience, length L4 is preferably a minimum value determined from the viewpoint of allocating the wiring space for the fingerprint sensor 42 and factors such as, for example, molding conditions of the resin portion 50. For example, length L4 may be adapted to correspond to the length (the length in the Y direction) of a range (see Q1 in FIG. 7) that the user feels that the user is touching with the user's finger. In this case, length L4 is preferably 10 mm or less in view of the average size of thumbs. Alternatively, length L4 may be adapted to correspond to the length of contact range Q3 in the Y direction. In this case, length L4 is preferably 5 mm or less in view of the average size (width) of index fingers.

Here, length L1 is preferably long to some extent in view of enhancing ease of operation of the side key 40 by allocating a space where the finger traces, and thus length L1 is, for example, within a range between 13 mm and 20 mm inclusive. This is determined from the viewpoint of allocating the movement range for slide operation. Length L3 is a minimum value determined from factors such as, for example, molding conditions of the resin portion 50, and thus length L3 is, for example, within a range of 0.5 mm to 2 mm. When length L1 and length L3 are determined as described above, the optimum value of length L2 is determined depending on the optimum value of length L4 described above.

Note that there may be a case where it is difficult to use a fingerprint sensor 42 having the optimum value of length L2 from the viewpoint of versatility and cost of the component and other factors. Thus, length L2 of the fingerprint sensor 42 does not need to be the optimum value. Also, in this case, as long as L3 and L4 have the relationship of L3<L4, the effective area of the fingerprint sensor 42 may still be large (in other words, the insensitive area may be small) compared to the comparative example (see FIG. 4 and other figures) including a fingerprint sensor 42 having the same size.

Each embodiment has been described in detail up to this point; however, this disclosure is not limited to specific embodiments, but various modifications and changes may be made within the scope described in claims. In addition, all or some of the constituents in the foregoing embodiments may be combined.

For example, although the surface 401 of the side key 40 is flat (in other words, in parallel with the YZ plane) in the foregoing embodiments, the surface 401 of the side key 40 may have a portion slightly inclined with respect to the YZ plane.

In addition, although the side key 40 is provided at the side surface portion of the device in the foregoing embodiments, the side key 40 may be provided at the bottom surface portion of the device or the upper surface portion of the device (for example, a frame area around the top plate member 12).

In addition, although the electronic device 1 includes the display unit (liquid crystal panel unit 12b) in the foregoing embodiments, the display unit does not necessarily need to include a display unit. For example, the side key 40 may be incorporated in an in-vehicle electronic device. For example, the side key 40 may be provided on the console box or the steering wheel of a vehicle. In the case where the side key 40 is provided on a console box, the side key 40 may be deposed such that the longitudinal direction of the side key 40 is coincident with the vehicle front-rear direction. In this case, if the sensing unit 421 is displaced from the center of the side key 40 to the user side (rearward in the vehicle front-rear direction) in the longitudinal direction, the same effect may be achieved. In the case where the side key 40 is provided on a steering wheel, the side key 40 may be disposed such that the longitudinal direction of the side key 40 is coincident with the direction connecting the 12 o'clock position and the 6 o'clock position of the steering wheel, when viewed in the neutral position of the steering wheel from the user. In this case, if the sensing unit 421 is displaced from the center of the side key 40 to the near side of the 6 o'clock position in the longitudinal direction, the same effect may be achieved on ease of operation from the 6 o'clock position side by a finger of a hand holding the steering wheel (for example, a thumb). In this case, the functions of the processor 4 may be implemented by an in-vehicle computer, and the functions of the display unit may be implemented by an in-vehicle display unit (for example, a display for a multimedia system or a head-up display). Functions triggered by the slide operation of the side key 40 may include volume adjustment of an in-vehicle audio system and temperature adjustment of an in-vehicle air conditioner. In this case, the side key 40 and the in-vehicle computer may operate independently of the in-vehicle display unit.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An electronic device comprising:
    an operation unit being capable of receiving a push in operation and including a fingerprint sensor along a longitudinal direction of the operation unit; and
    a processor that performs fingerprint authentication processing and processing to respond to a movement of a finger of a user in the longitudinal direction on the operation unit, based on a detection result by the fingerprint sensor, wherein
    a sensing unit of the fingerprint sensor is displaced from a center of the operation unit in the longitudinal direction.

2. The electronic device according to claim 1, further comprising a display unit on one surface of a housing of the electronic device, wherein
    the operation unit is configured to be pressed from a side surface of the housing, the side surface defined with respect to the one surface, and the longitudinal direction of the operation unit is perpendicular to a direction of the push-in operation, and screen control processing in the display unit is executed based on the movement of the finger in the longitudinal direction.

3. The electronic device according to claim 2, wherein
    the screen control processing includes at least one of scroll processing to scroll an image in the screen, transition processing to cause screen transition, and zoom-in and zoom-out processing to zoom in and out on an image in the screen.

4. The electronic device according to claim 2, wherein
    the operation unit is provided on a side surface of the electronic device.

5. The electronic device according to claim 1, wherein
    the operation unit is provided on a side surface of the electronic device, and
    the operation unit is capable of positional change in a direction perpendicular to the side surface.

6. The electronic device according to claim 5, wherein
    the processor further performs processing to respond to the positional change of the operation unit.

7. The electronic device according to claim 1, wherein
    the operation unit includes a resin portion in which the fingerprint sensor is embedded.

8. The electronic device according to claim 7, wherein
    the fingerprint sensor is in a form of a chip, is mounted on a circuit board, and is electrically connected to an electrode on the circuit board on a side opposite in the longitudinal direction to a side to which the sensing unit is displaced.

9. The electronic device according to claim 1, wherein
    a distance between the fingerprint sensor and an edge of the operation unit in the longitudinal direction is equal to or less than 10 mm in the longitudinal direction.

* * * * *